(12) United States Patent
Gnauert

(10) Patent No.: US 8,695,400 B2
(45) Date of Patent: Apr. 15, 2014

(54) SYSTEM AND METHOD FOR DETERMINING READINGS OF GASES AND/OR AN AEROSOL FOR A MACHINE

(76) Inventor: Uwe Gnauert, Blieskastel (DE)

( * ) Notice: Subject to any disclaimer, the term of this patent is extended or adjusted under 35 U.S.C. 154(b) by 0 days.

(21) Appl. No.: 13/261,512

(22) PCT Filed: Feb. 9, 2011

(86) PCT No.: PCT/EP2011/051885
§ 371 (c)(1),
(2), (4) Date: Feb. 5, 2013

(87) PCT Pub. No.: WO2011/141191
PCT Pub. Date: Nov. 17, 2011

(65) Prior Publication Data
US 2013/0125624 A1    May 23, 2013

(30) Foreign Application Priority Data

May 14, 2010   (EP) .................................. 10162870

(51) Int. Cl.
*G01N 21/01*   (2006.01)

(52) U.S. Cl.
USPC .......................................... 73/23.33; 356/438

(58) Field of Classification Search
USPC ........................... 73/23.33; 356/436, 437, 438
See application file for complete search history.

(56) References Cited

U.S. PATENT DOCUMENTS

| | | | |
|---|---|---|---|
| 3,207,026 A | | 9/1965 | Churchill et al. |
| 4,544,273 A | * | 10/1985 | Berndt .......................... 356/434 |
| 4,633,706 A | * | 1/1987 | Ito et al. ...................... 73/23.33 |
| 5,807,750 A | * | 9/1998 | Baum et al. .................... 436/164 |
| 6,137,582 A | * | 10/2000 | Stedham ........................ 356/436 |
| 6,369,890 B1 | | 4/2002 | Harley |
| 7,345,766 B2 | * | 3/2008 | Schindler et al. .............. 356/440 |
| 7,932,490 B2 | * | 4/2011 | Wang et al. .................... 250/287 |
| 8,107,080 B2 | * | 1/2012 | Socha et al. ................... 356/436 |
| 8,184,296 B2 | * | 5/2012 | Johns et al. .................... 356/437 |
| 8,531,671 B1 | * | 9/2013 | Hansen ........................ 356/438 |
| 2011/0232268 A1 | * | 9/2011 | Nelson ............................ 60/276 |
| 2011/0232362 A1 | * | 9/2011 | Thiagarajan et al. ......... 73/23.33 |

(Continued)

FOREIGN PATENT DOCUMENTS

| | | |
|---|---|---|
| CH | 349 831 A | 10/1960 |
| DE | 26 08 390 A1 | 8/1977 |

(Continued)

OTHER PUBLICATIONS

English language machine translation of WO2007140640 description obtained on Sep. 19, 2013 from <http://www.epo.org/>.*

*Primary Examiner* — Lisa Caputo
*Assistant Examiner* — Punam Roy
(74) *Attorney, Agent, or Firm* — George Pappas

(57) ABSTRACT

In order to improve a system for monitoring the working area atmosphere of an operating engine, measuring devices (2) for determining readings for a gas and/or an aerosol in the working area (4) of an operating engine are used as a starting point. Each measuring device comprises a suction means (8) which extracts a gas and/or a mixture of an aerosol from the working area (4) of the operating engine and feeds it to a sensor unit (16, 17, 18). An electronics module for operating the sensor unit (16, 17, 18) is also present. The suction means is designed as a convection pump (8) preferably with a heating device (42) and a cooling device (44).

20 Claims, 6 Drawing Sheets

(56) References Cited

U.S. PATENT DOCUMENTS

| | | | |
|---|---|---|---|
| 2011/0310391 A1* | 12/2011 | Janssen et al. | 356/438 |
| 2012/0096925 A1* | 4/2012 | Hansen et al. | 73/28.04 |
| 2012/0304738 A1* | 12/2012 | Landkammer | 73/23.33 |

FOREIGN PATENT DOCUMENTS

| | | |
|---|---|---|
| DE | 239 474 A1 | 9/1986 |
| EP | 0 071 391 | 2/1983 |
| EP | 0 777 041 A2 | 4/1997 |
| GB | 2 166 232 A | 4/1986 |
| JP | 57-134309 | 8/1982 |
| JP | 09-229831 A | 9/1997 |
| JP | 11-326179 A | 11/1999 |
| JP | 2000-503120 A | 3/2000 |
| JP | 2001-500206 A | 1/2001 |
| JP | 2005-030945 A | 2/2005 |
| JP | 2005-338022 A | 12/2005 |
| WO | WO 97/25611 A2 | 7/1997 |
| WO | WO 98/11331 | 3/1998 |
| WO | WO 98/11331 A1 | 3/1998 |
| WO | WO 2007/140640 A2 | 12/2007 |

* cited by examiner

SYSTEM AND METHOD FOR DETERMINING READINGS OF GASES AND/OR AN AEROSOL FOR A MACHINE

This application claims priority from PCT Application No. PCT/EP2011/051885 filed Feb. 9, 2011 which claims priority from European Application No. EP 10162870.9 filed on May 14, 2010, which applications are incorporated herein by reference.

TECHNICAL FIELD

The invention relates to a system with measuring devices for determining readings of gases and/or an aerosol for an operating engine and to a monitoring method by means of which readings of gases and/or an aerosol in an operating engine, in particular readings of the aerosol concentration in an internal combustion engine, are determined.

BACKGROUND OF THE INVENTION

The monitoring of gases and aerosol concentrations, particularly of lubricating oil mist in working areas of internal combustion engines or in casings of power transmission gears, is of considerable interest for avoiding damages. A rapid increase of the oil mist concentration is indicative of damages, for example of the tearing off of a lubricating film. As a result of frictional heat thus formed, oil vapors are formed which condensate to oil mist in the working area and thus result in a rapid increase of the oil mist concentration. If the resulting hazard is quickly recognized, then explosions and a concomitant threat to persons and further damages to the operating engine can be prevented with appropriate counteractions such as shutting down of the operating engine or of individual components of the operating engine. However, it is also possible to study specific gas components in such a working atmosphere by means of other sensors.

Furthermore, in addition to the tearing off of the lubricating film, so-called blow-throughs may occur between the piston and the associated cylinder wall in bearings of piston engines due to damaged piston rings, which cause a total damage of the piston/cylinder aggregate ("piston seizure"). An increase of the oil mist density with simultaneous rise in temperature due to the hot combustion gases is indicative of such blow-throughs.

First approaches for measuring the oil mist concentration are known from EP-A-0 071 391. In EP-A-0 071 391 it is suggested to draw the aerosol from the working area through a measuring compartment by means of a winged wheel blower and to carry out therein a reflection measurement by means of a radiation source and a radiation sensor. The winged wheel blower suggested therein is intended for use with a plurality of compartments arranged parallel to each other.

The disadvantages of such an arrangement were already shown in WO-A-98/11331. In addition to the considerable constructive and operating expenses of such arrangement, the use of a blower for drawing out has been found to be insufficient, meaning that such a solution should be avoided. Moreover, the drawing out operation also draws dirty air through the pipe system, and thus oil accumulations in the form of oil bags can form which clog the lines, thus rendering the operation of the measuring device difficult or impossible.

In contrast thereto, in DD-A-239 474 and in GB-A-2 166 232 it is suggested to arrange, for each working area of the driving gear of an internal combustion engine, a sensor unit directly in the interior of the respective working area and to connect it via an optical or electrical transmission path to an evaluation unit arranged outside of the internal, combustion engine. However, such a solution is associated with the disadvantage that the base concentration of oil mist and splash oil in the long run contaminates the sensors and, therefore, also leads to false alarms.

In contrast, in the already mentioned WO-A-98/11331 it is suggested to provide, in each working area to be monitored, a sensor unit with an extraction based on a venturi nozzle. Such a measuring device operates without mechanically moving parts and is, therefore, almost wearless. However, it has been found that the air flow generated solely by the crank movement of the crankshaft cannot produce a sufficient perfusion of the vacuum suction nozzle, so that the effectivity of the measuring device is not ensured. In WO 2007/140640 A it was suggested to provide a common external compressed air supply for supplying all of the venturi nozzles of an engine and to ensure supply to the individual measuring points with appropriate supply lines. However, this approach has the disadvantage of requiring complex supply lines.

From DE 26 08 390 A1 it is generally known that a measuring device for indicating the formation of oil mist—and/or oil smoke in engine rooms of internal combustion engines can be configured with an air jet pump, with DE 26 08 390 A1 suggesting to have all of the sampling lines lead into a common collection chamber. But in this manner a differentiated monitoring of the combustion room by means of multiple measuring points, which would allow for localization of the damage site, is not possible.

SUMMARY OF THE INVENTION

It is an object of the invention to provide an improved system with measuring devices of the above mentioned type for determining readings of a gas and/or aerosol for an operating engine. In doing so, the various samples taken shall remain unmixed with each other. On the other hand, the individual measuring points shall be supplied with only a single cable. Furthermore, it appears essential that no moving parts such as a rotary blower etc. with reduced acceptance regarding the atmosphere of the working area of an internal combustion engine shall be used.

Here, the measures of the invention initially have the result that without moving parts, at least without a propeller that can quickly become contaminated by the atmosphere of an internal combustion engine, an analysis of the gas mixture and/or of an aerosol from the working area can be achieved with only a single electrical supply line.

For the analysis of an aerosol it is customary to use an optical sensor. Generally, it is possible for the convection pump to have only one heating device or one cooling device. However, a good circulating performance is achieved by having a heating device plus a cooling device. In this case the sensor unit or a plurality of sensor units, respectively, are arranged in the flow channel between the heating device and the cooling device.

In an advantageous embodiment, the heating element of the heating device is configured e.g. as a conventional resistive heating or as an inductive heating, and the cooling element of the cooling device is configured as a passive heat exchanger against the environment. Thereby, the device has to be configured in such a way that the ambient temperature allows for a sufficient temperature difference.

An alternative embodiment is provided by a conventional heating element and a peltier element as the cooling element, wherein the peltier element is used for cooling, and the— warm—counter side of the peltier element is coupled to the environment via a heat exchanger.

Furthermore, it is possible to realize the heating device and the cooling device of the convection pump by means of a peltier element for heating the gas or aerosol/gas mixture of the sensor unit and for cooling behind the sensor unit.

In all of these embodiments, the suction point and the recovery point will advantageously be adjacent to each other. The flow channel can be configured as two concentrically arranged pipes, in which case the suction point and the recovery point are concentrically arranged.

If only one heating device or one cooling device is provided, the suction point can be arranged above the recovery point, in which case the convection pump comprises a cooling device, or else the suction point can be arranged below the recovery point, in which case the convection pump comprises a heating device.

Through the advantageous embodiment of a flow channel it will be possible in many cases to avoid having a separation means for separating off coarse components, but otherwise such separation means—a so called pipe or a labyrinth for separating off, in particular, oil droplets from the oil mist can be provided before the sensor.

It is advantageous to have a temperature sensor arranged in the flow channel. In a simple embodiment, a temperature sensor is arranged in the heating side of the flow channel and the system comprises a device for warning when the temperature measured by the temperature sensor is excessive. At a temperature of for example 150° the system will issue a warning and optionally the engine will be checked. It is even more advantageous to provide two temperature sensors for monitoring the temperature difference between the heating side and the cooling side of the flow channel. In this manner the temperature difference, which represents a measure for the flow and accordingly a monitoring value therefor, can be used as a criterion for a sufficient flow. In a further development, a controlling device is provided for controlling the power of the heating element and the cooling element by means of the temperature difference, the temperature in the heating side or the temperature in the cooling side of the flow channel.

The aforementioned elements as well as those claimed and described in the following exemplary embodiments, to be used according to the invention, are not subject to any particular conditions by way of exclusion in terms of their size, shape, use of material and technical design, with the result that the selection criteria known in the respective field of application can be used without restrictions.

BRIEF DESCRIPTION OF THE DRAWINGS

Further details, advantages and features of the object of the present invention will become apparent from the following description and the corresponding drawings, in which measuring devices according to the present invention are illustrated by way of example. The drawings show.

DETAILED DESCRIPTION OF THE PREFERRED EMBODIMENTS

Figure 1:
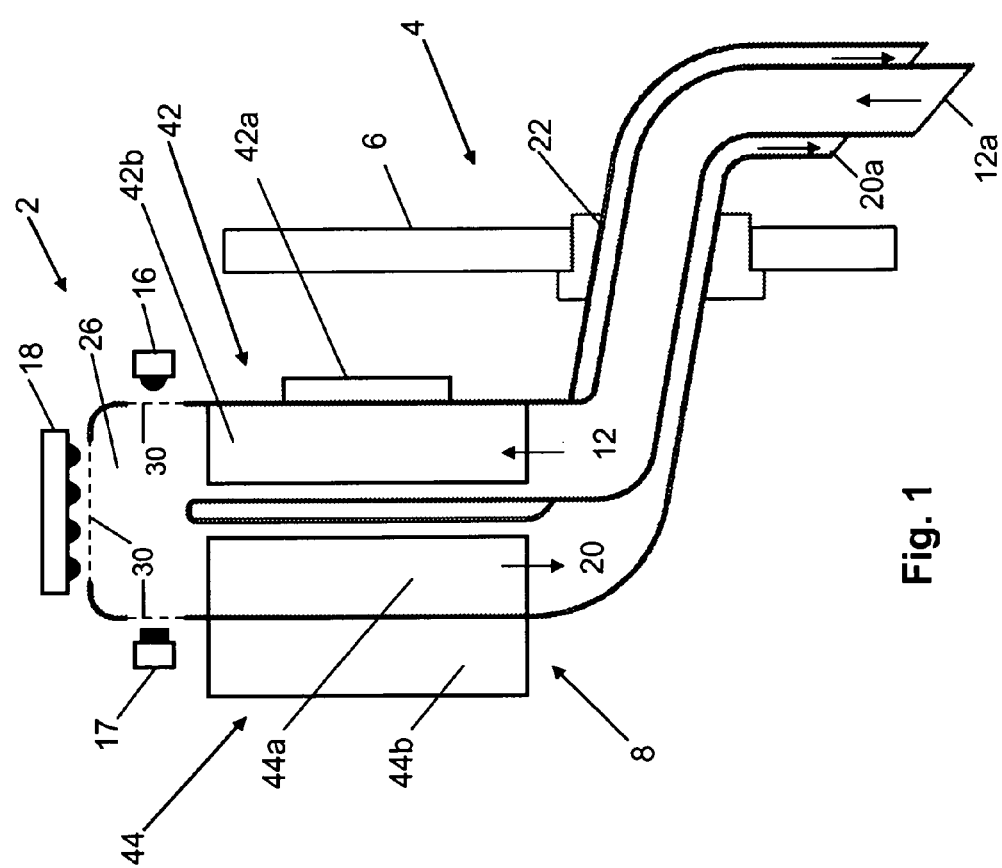
FIG. 1 a schematic view of a measuring device in the working area of an internal combustion engine according to a first embodiment of the present invention, with a conventional heating device and a cooling device with a passive heat exchanger that conducts away the heat to the environment.
Figure 4:
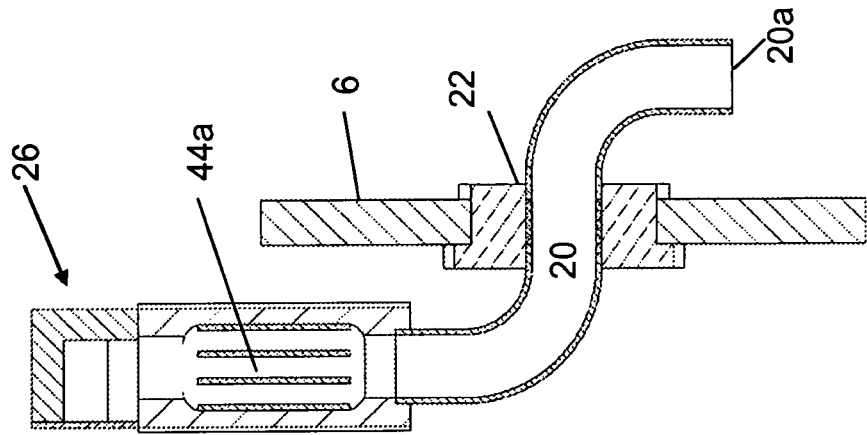
FIG. 4 the measuring device according to FIG. 1 as a sectional view taken from the side with a view onto the fins of the heat exchanger in the flow channel.
Figure 3:
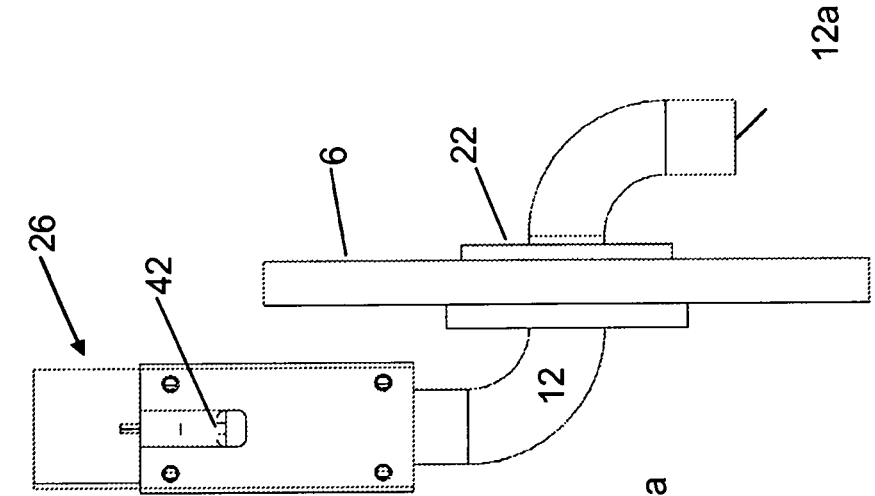
FIG. 3 a side view of the measuring device according to FIG. 1.
Figure 2:
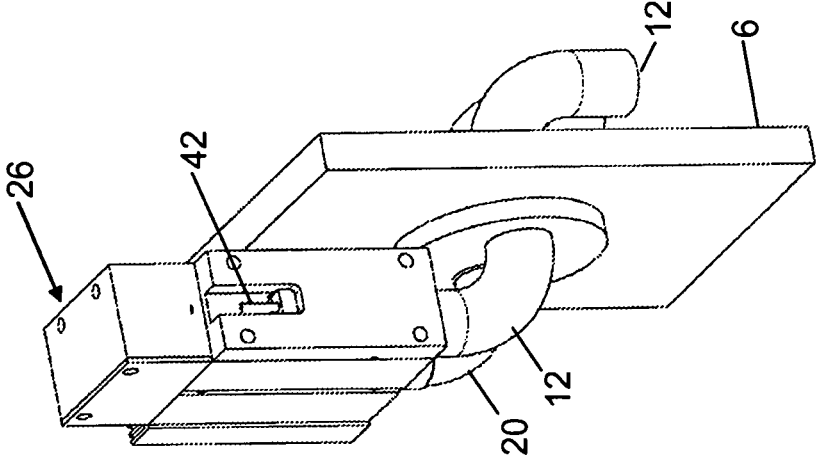
FIG. 2 the measuring device according to FIG. 1 in a perspective view from the side.

The FIGS. 1 to 4 show a measuring device 2 of the system according to a first embodiment of the present invention. The measuring device is built by means of a flange 22 into the wall 6 of the operating engine, in the present case into the working area 4 of an internal combustion engine. The flange 22 comprises a feed line 12 for a gas/aerosol mixture which is drawn in from the working area 4 by the pumping action of a convection pump 8, and which is again fed back into the working area 4 by means of a recovery line 20.

In the present embodiment, the recovery line 20 is arranged close to the feed line 12 and, therefore, the suction point 12*a* and the recovery point 20*a* of the gas/aerosol mixture are located close to each other.

The two lines 12, 20—as seen from the suction point and recovery point, respectively, and starting out from the flange—initially comprise a substantially horizontal section, which—after a bent section—leads into the actual convection pump area.

The latter comprises in the feed line 12 thereof a heating device 42 with a resistive heating element 42*a* and a heat exchanger 42*b*, and in the recovery lines 20 thereof a cooling device 44 with a heat exchanger 44*a* in the recovery line and a further heat exchanger 44*b* that conducts the heat to the environment.

By means of the heating device 42 with the resistive heating element 42*a* and the heat exchanger 42*b* the gas/aerosol mixture is heated up within the feed area 12 and due to its concomitant expansion rises up into the actual measuring region 26. On the other hand the gas/aerosol mixture that has already been measured is cooled down in the recovery area by means of the cooling device 44 with the heat exchangers 44*a* and 44*b* and contracts, which leads to an amplification of the above mentioned current all the way to the recovery point in the working area of the internal combustion engine.

This embodiment stands out in that it needs only a single active thermal element, namely, a conventional heating element. In this manner, this embodiment is not only very easy to set up and also easily operated without much effort, but also particularly reliable.

In the present embodiment, the actual measuring region comprises a transmission light measuring path on the one hand and a scattered light measuring path on the other hand. The transmission light measuring path is implemented with the light source 17, namely a light emitting diode, and the optical sensor 16; the light intensity transmitted of the light source 17 is measured. The scattered light path is implemented by the light source 18 and by the sensor 16 also used for the transmission light path; the light scattered from the aerosol present in the light path is measured. The measurement of transmission and scattered light with only one sensor is carried out intermittently in time. The sensor and the light source, respectively, are coupled to the measuring area by means of optical windows 30 that are adapted to the optical properties of the sensors and the light source, respectively.

The temperature of the heating side can be regulated via the heating power of the resistive heating depending on the temperature of the cooling side in such a manner that—at least over a wide region of ambient temperatures and temperatures of the working area—there is a constant temperature difference between the heating side and the cooling side, which difference can be e.g. 50° C., i.e. at 45° C. and 70° C., respectively, on the cooling side, the temperature of the heating side is 95° C. and 120° C., respectively. A minimum temperature difference between the heating and the cooling side shall be maintained to ensure a sufficient flow. If the temperature difference falls short of this, an alarm can be triggered.

As typical values for the embodiment described herein, the heating device will have an average supplied power of about 5 watts and a normal working temperature of 120° C. The diameter of the feed line is about 15 to 20 mm.

Figure 5:
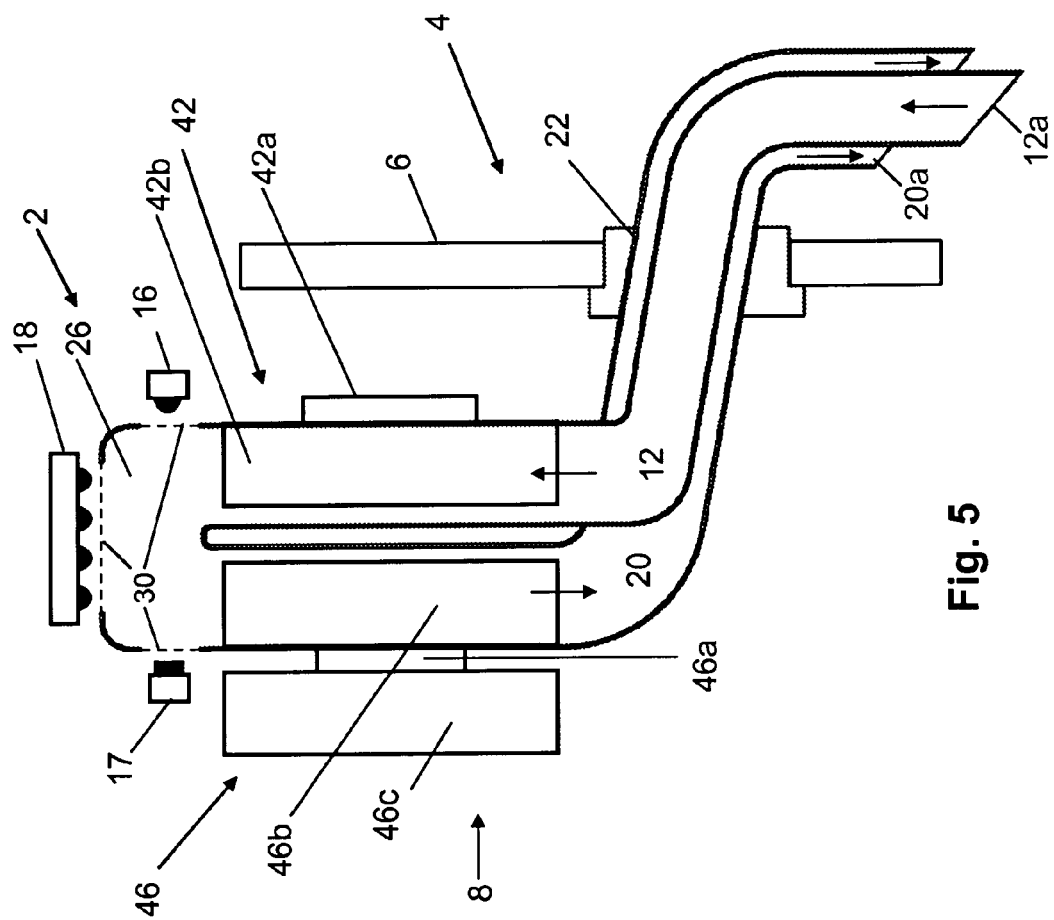
FIG. 5 a schematic view of an alternative embodiment of the measuring device with a conventional heating device and an active cooling device that conducts away the heat via a peltier element and a heat exchanger to the environment.
Figure 8:
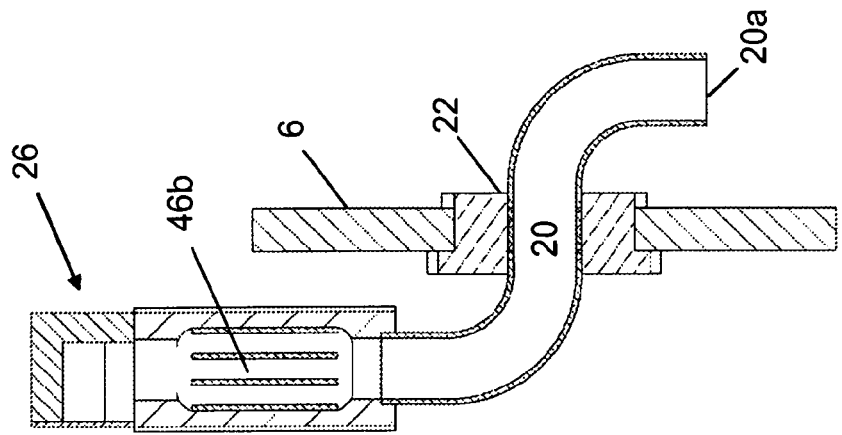
FIG. 8 the measuring device according to FIG. 5 as a sectional view taken from the side with a view onto the fins of the heat exchanger in the flow channel.
Figure 7:
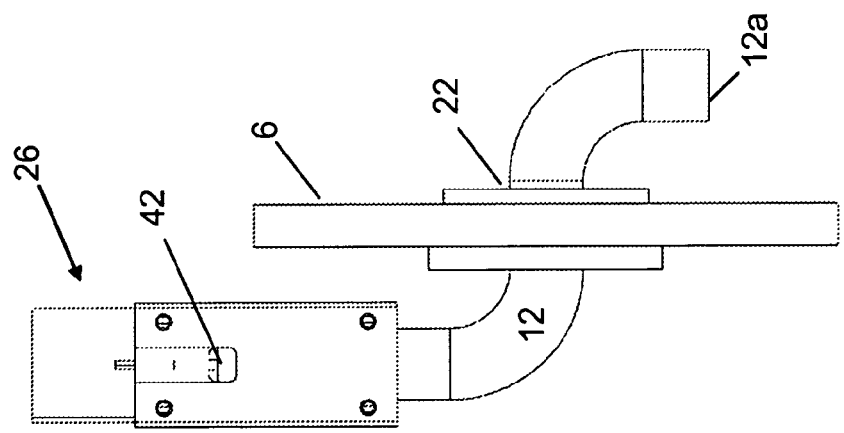
FIG. 7 a side view of the measuring device according to FIG. 5.
Figure 6:
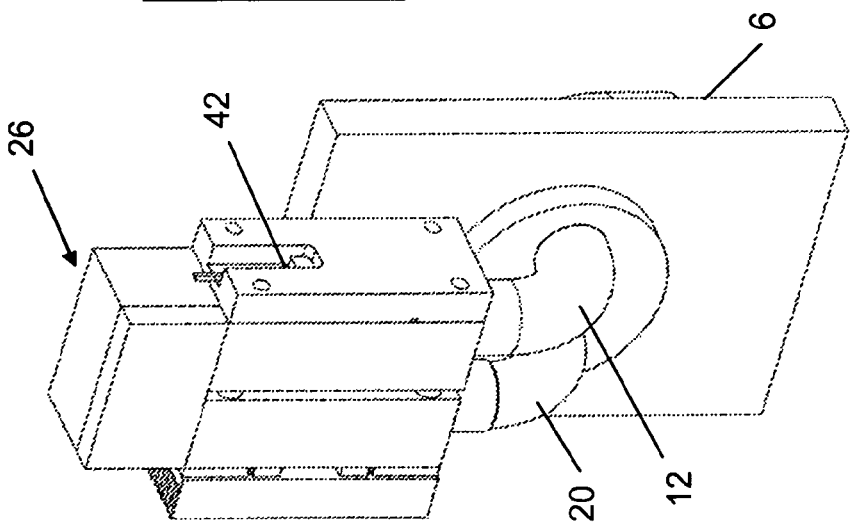
FIG. 6 the measuring device according to FIG. 5 in a perspective view taken from the side.
Figure 9:
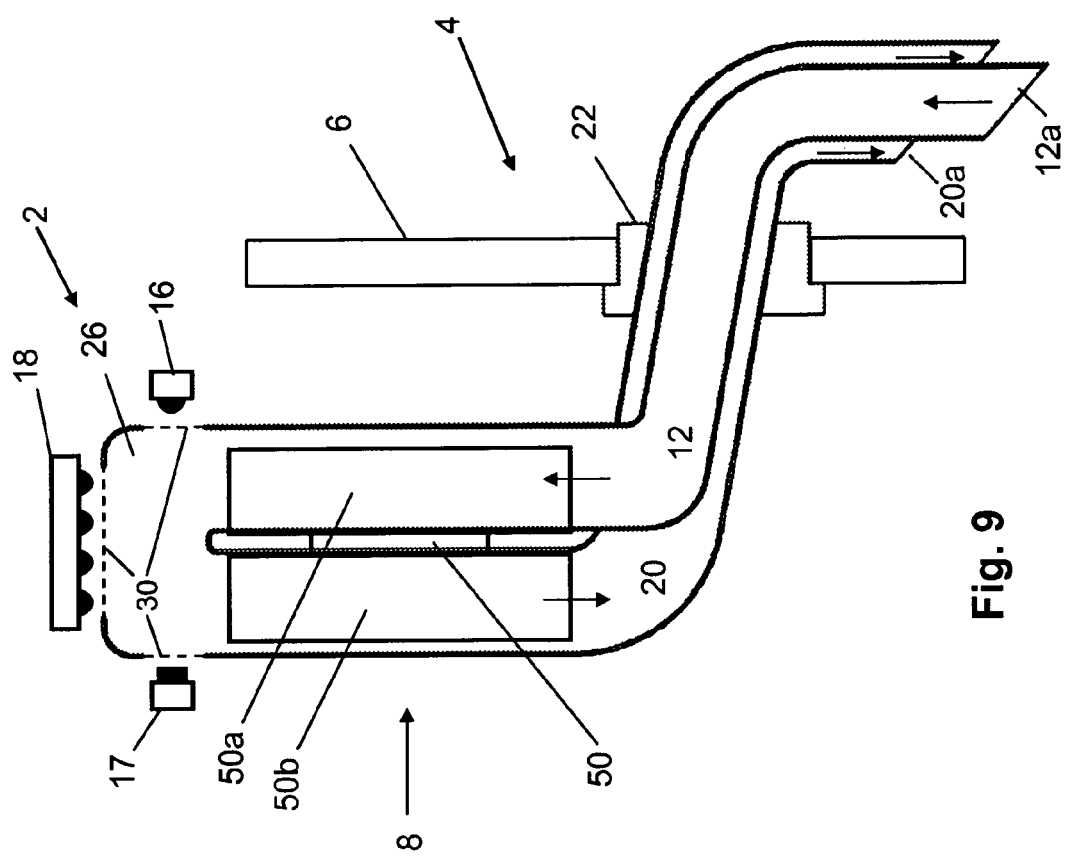
FIG. 9 a schematic view of a further, third embodiment of the measuring device with a heating device and a cooling device that is configured via a peltier element (heating pump) between the heat exchangers of the heating side and the cooling side of the flow channel.
Figure 12:
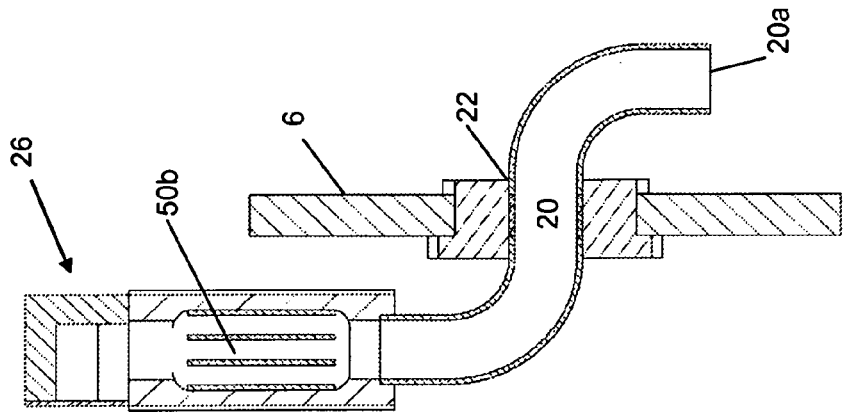
FIG. 12 the measuring device according to FIG. 9 as a sectional view taken from the side with a view onto the fins of the heat exchanger in the flow channel.
Figure 11:
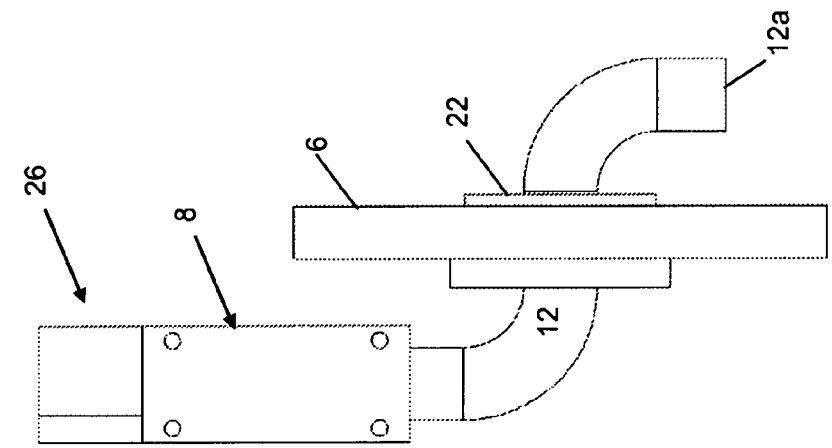
FIG. 11 a side view of the measuring device according to FIG. 9.
Figure 10:
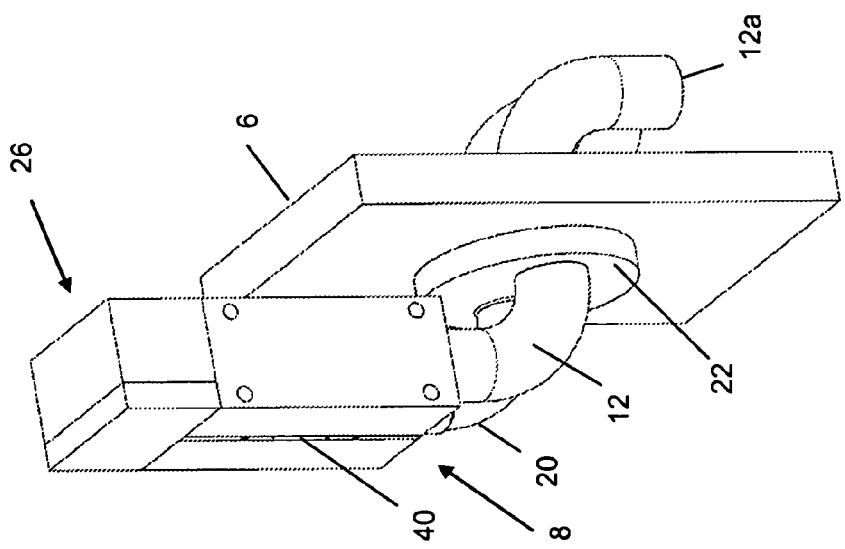
FIG. 10 the measuring device according to FIG. 9 in a perspective view taken from the side.

The FIGS. 5 to 8 show an alternative embodiment that again comprises a heating device 42 with a conventional heating element 42a that is also configured as an electrical resistive heating and a heat exchanger 42b and an active cooling device 46, this embodiment comprising a peltier element 46a with a heat exchanger 46b coupled thereto and a heat exchanger 46c coupled to the environment. The feed and recovery of the heat of the gas/aerosol mixture, respectively, occurs via the heat exchangers 42b, 46b.

The heating device is again configured in such manner that the inflowing gas/aerosol mixture reaches a temperature of e.g. 120° C. The cooling element in this embodiment is configured so that the gas/aerosol mixture flowing back which has already been analyzed is cooled down to a temperature of about 30° C. so that a convection flow is maintained. The heating side of the peltier element in this embodiment reaches a temperature of about 60°. This embodiment has the advantage that the ambient temperatures are higher and that the temperature difference between the heating side and the cooling side can be chosen larger in favor of a higher pump power, although this requires a larger expenditure for the cooling performance.

In a further embodiment according to the FIGS. 9 to 12 both the heating and the cooling are achieved with a peltier element 50 coupled to the heating and to the cooling by means of heat exchanger elements 50*a* and 50*b*. In this embodiment the peltier element 50 is arranged in the middle between the adjacent feed line and recovery line 12, 20 and thermally coupled to the feed line 12 and recovery line 20 by means of two heat exchangers 50*a*, 50*b*—which in the present embodiment are aluminum strip profiles with a size of 50×29×25 mm. The peltier element 50 is arranged in such a manner that its heating side cooperates thermally with the feed by means of the heat exchanger 50*a* and that its cooling side cooperates thermally with the recovery by means of the heat exchanger 50*b*.

As a typical value for this embodiment, the peltier element 40 will have an average power supplied of about 5 watt, a maximum temperature of 150° C. and a size of 20×20×3.6 mm. The diameter of the feed line is about 15 to 20 mm, and the operating temperature of the heat exchanger elements 50*a*, 50*b* is 50 to 60° C. on the heating side and 30° C. on the cooling side, which is above the gas/aerosol temperature in the working area.

LIST OF REFERENCE NUMERALS

2 measuring device
4 working area
6 wall of the operating engine
8 convection pump
12 gas/aerosol feed line
12*a* suction point
16 sensor
17 transmission light source for the sensor
18 scattered light source for the sensor
20 gas/aerosol recovery
20*a* recovery point
22 flange
26 measuring region
30 optical windows
42 heating device
42*a* heating element
42*b* heat exchanger for the heating device, coupled to the gas/aerosol
44 cooling device
44*a* heat exchanger for the cooling device, coupled to the gas/aerosol
44*b* heat exchanger for the cooling device, coupled to the environment
46 cooling device with peltier element
46*a* peltier element
46*b* heat exchanger for the cooling device, coupled to the gas/aerosol and to the peltier element
46*c* heat exchanger for the cooling device, coupled to the environment and to the peltier element
50 peltier element
50*a* heat exchanger for the heating device, coupled to the gas/aerosol
50*b* heat exchanger for the cooling device, coupled to the gas/aerosol

The invention claimed is:

1. A system for monitoring the working area atmosphere of an operating engine, in particular in the working area of an internal combustion engine, by the arrangement of at least one measuring device for determining readings for a gas and/or an aerosol in the working area of the operating engine, wherein the system comprises a flow channel that is connected with the working area at a suction point for drawing in a gas or an aerosol/gas mixture from the working area of the operating engine and at a recovery point for feeding back the gas or the aerosol/gas mixture into the working area of the machine, wherein a sensor unit for determining the readings is arranged in a measuring region of the flow channel, and an electronics device is associated to the operation of the sensor unit, characterized in that in the flow channel there is arranged a convection pump, wherein the convection pump comprises at least one heating device and/or cooling device.

2. The system according to claim 1, characterized in that the sensor unit comprises at least one optical sensor for aerosol analysis.

3. The system according to claim 1, characterized in that the system comprises a heating device and a cooling device.

4. The system according to claim 3, characterized in that the measuring region is arranged in the flow channel between the heating device and the cooling device.

5. The system according to claim 4, characterized in that the heating device of the convection pump comprises an electrical resistance element or an electrical inductive element and a heat exchanger before the sensor unit for heating the gas or the aerosol/gas mixture, and that the cooling device of the convection pump comprises a passive heat exchanger with a thermal connection to the environment for cooling the gas or the aerosol/gas mixture behind the sensor unit.

6. The system according to claim 4, characterized in that the heating device of the convection pump comprises an electrical resistance element or an electrical inductive element and a heat exchanger in front of the sensor unit for heating the gas or the aerosol/gas mixture, and that the cooling device of the convection pump comprises a cooling device for the gas or the aerosol/gas mixture behind the sensor unit, with a peltier element and a heat exchanger with a thermal connection to the gas or the aerosol/gas mixture to be cooled and a heat exchanger with a thermal connection to the environment.

7. The system according to claim 4, characterized in that the heating device and the cooling device of the convection pump are configured with a peltier element and heat exchangers, wherein a heat exchanger for heating is arranged in front of and a heat exchanger for cooling is arranged behind the sensor unit of the gas or aerosol/gas mixture, and wherein one side of the peltier element is coupled to the heat exchanger for heating and the other side of the peltier element is coupled to the heat exchanger for cooling.

8. The system according to claim 1, characterized in that the suction point and the recovery point are adjacent to each other.

9. The system according to claim 1, characterized in that the flow channel in the region of the feed and the recovery is formed by means of two concentrically arranged pipes.

10. The system according to claim 8, characterized in that the suction point and the recovery point are concentrically arranged.

11. The system according to claim 1, characterized in that the suction point is arranged above or below the recovery point, the convection pump comprising a cooling element and a heating element, respectively.

12. The system according to claim 1, characterized in that the flow channel further comprises separation means for separating off coarse components, particularly oil droplets, from the oil mist.

13. The system according to claim 1, characterized by at least one temperature sensor arranged in the flow channel, wherein the at least one temperature sensor is preferably arranged in the heating side of the flow channel, and wherein the system comprises a warning device that triggers a warning or an alarm when a threshold temperature value is exceeded.

14. The system according to claim 13, characterized in that two temperature sensors for monitoring the temperature difference between the heating side and the cooling side of the flow channel are provided.

15. The system according to claim 13, characterized by a controlling device for controlling the power of the heating element and the cooling element by means of the temperature difference, the temperature at the heating side or the temperature at the cooling side of the flow channel.

16. The system according to claim 2, characterized in that the system comprises a heating device and a cooling device.

17. The system according to claim 16, characterized in that the measuring region is arranged in the flow channel between the heating device and the cooling device.

18. The system according to claim 17, characterized in that the heating device of the convection pump comprises an electrical resistance element or an electrical inductive element and a heat exchanger before the sensor unit for heating the gas or the aerosol/gas mixture, and that the cooling device of the convection pump comprises a passive heat exchanger with a thermal connection to the environment for cooling the gas or the aerosol/gas mixture behind the sensor unit.

19. The system according to claim 17, characterized in that the heating device of the convection pump comprises an electrical resistance element or an electrical inductive element and a heat exchanger in front of the sensor unit for heating the gas or the aerosol/gas mixture, and that the cooling device of the convection pump comprises a cooling device for the gas or the aerosol/gas mixture behind the sensor unit, with a peltier element and a heat exchanger with a thermal connection to the gas or the aerosol/gas mixture to be cooled and a heat exchanger with a thermal connection to the environment.

20. The system according to claim 17, characterized in that the heating device and the cooling device of the convection pump are configured with a peltier element and heat exchangers, wherein a heat exchanger for heating is arranged in front of and a heat exchanger for cooling is arranged behind the sensor unit of the gas or aerosol/gas mixture, and wherein one side of the peltier element is coupled to the heat exchanger for heating and the other side of the peltier element is coupled to the heat exchanger for cooling.

* * * * *